(12) United States Patent
Song et al.

(10) Patent No.: US 8,623,292 B2
(45) Date of Patent: Jan. 7, 2014

(54) DEHYDRATION SENSORS WITH ION-RESPONSIVE AND CHARGED POLYMERIC SURFACTANTS

(75) Inventors: Xuedong Song, Alpharetta, GA (US); Ning Wei, Roswell, GA (US); Ronnie L. Phillips, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 650 days.

(21) Appl. No.: 12/858,204

(22) Filed: Aug. 17, 2010

(65) Prior Publication Data

US 2012/0042722 A1   Feb. 23, 2012

(51) Int. Cl.
 *G01N 33/48* (2006.01)
(52) U.S. Cl.
 USPC .......................................... 422/420; 422/400
(58) Field of Classification Search
 USPC .................................. 422/420, 400
 See application file for complete search history.

(56) References Cited

U.S. PATENT DOCUMENTS

| | | |
|---|---|---|
| 5,403,744 A | 4/1995 | Zimmerle |
| 2006/0137434 A1 | 6/2006 | Cohen et al. |
| 2009/0157024 A1 | 6/2009 | Song |
| 2010/0159599 A1 | 6/2010 | Song et al. |

*Primary Examiner* — Monique Cole
(74) *Attorney, Agent, or Firm* — Denise L. Stoker; Vincent T. Kung (57) ABSTRACT

A lateral flow assay device for determining the relative ionic strength of urine is described. The device includes a buffering zone having a polyelectrolyte disposed therein, and an indicator zone having a pH indicator non-diffusively immobilized therein, the indicator zone being separate from the buffering zone and positioned adjacent to and in fluid communication with the buffering zone. A detection zone is part of the buffering zone, and has a buffering component comprising a weak polymeric acid and weak polymeric base with a pKa $\leq 10^{-3}$, and a class of charged polymeric surfactants that are responsive to relative ion concentrations in a sample solution, and a charged pH indicator with a charge opposite to that of the charged polymeric surfactant. The charged polymeric surfactant is soluble in amounts of greater than or equal to about 1% by weight ($\geq$1 wt. % solute) in water and aqueous solutions of low ionic concentration of $\leq$0.1 wt. % salts, but insoluble (<1 wt. % solute) in aqueous solution of high ionic concentrations of >0.1 wt. % salts. The present invention also describes absorbent articles incorporating such an assay device and methods of monitoring dehydration or testing ion strength of a urine sample using such a test format.

8 Claims, 3 Drawing Sheets

DEHYDRATION SENSORS WITH ION-RESPONSIVE AND CHARGED POLYMERIC SURFACTANTS

FIELD OF INVENTION

The present invention pertains to a dehydration sensor and the absorbent products containing the sensor. In particular, the invention pertains to a sensor that can monitor a user's hydration status.

BACKGROUND

Dehydration is the depletion of fluids and associated electrolytes from the body. Normally, a person's daily, total fluid amount is regulated to be within about ±0.02% of body weight, and water in the body may comprise approximately 63% of the entire body mass. A balance of bodily fluids is achieved and maintained by matching the input and excretion of liquid from the body, and an imbalance in fluids can be linked to either dehydration or hypohydration. Dehydration can be of particular concern for either the infirm, elderly, or infants, and can have serious consequences to a dehydrated person if not cared for properly. Loss of body fluids in amounts of less than about 2-5% body mass have been associated with reduced heat dissipation, loss of cardiovascular function, and decreased physical stamina.

Specific gravity of an individual's urine is a routinely measured means of evaluating the relative hydration status of the individual. Determination of urine volume and electrolyte concentrations can aid in monitoring whether the individual's body fluid amounts are in balance. Urine specific gravity (USG) refers to the ratio of the density of urine to the density of water. USG is affected mainly by the solids and ions in urine. USG correlates proportionally with the solid concentration and ion concentration of urine. USG normally ranges from 1.002 to 1.030. It is accepted that USG<1.020 is considered to be well hydrated, USG between 1.020 and 1.025 is considered to be semi-dehydrated and USG>1.025 is considered to be severely dehydrated. USG can be measured by an instrument such as either a urinometer or urine test dipsticks or strips. Modern dipsticks are commonly based on lateral flow assay technology. Three major methods, namely refractometry, hydrometry and reagent strips, are commonly used for USG measurements. Although refractometry and hydrometry are very accurate, they require special instruments and trained persons to operate.

Over the years, various manufacturers have attempted different methods to improve the performance of the dipsticks for specific gravity, such as different formulations to increase sensitivity and specificity. Problems, however, persist for all the commercially available dipsticks. A major problem is that the user has to read a change in color within a few brief minutes after dipping in the sample because the color development is not stable under test conditions. The signals that one may observe outside of the time window are often inaccurate, hence normally invalid. For some analyte tests, such as ion concentration in urine (i.e., specific gravity for dehydration), a certain time period is needed before a signal is fully developed and a valid reading can be achieved. This situation may not be a problem for a test that a user can constantly monitor; however, it becomes a problem when constant monitoring of the test is not feasible and sample introduction time is uncertain. For instance, it is difficult, if not impossible, to predict accurately when a baby or incontinent adult will urinate to provide a sample for an assay device in a diaper or other personal care product. Therefore, the assay device requires a validation mechanism to make sure that a reading is within the valid reading time window.

In recent years, reagent strips have become more popular, particularly in the over-the-counter and point-of-care markets, mainly due to their low cost and ease of use. In general, conventional reagent strips change color in response to the ionic strength of a urine sample. The ionic strength of urine is a measure of the amount of ions present in the urine. The USG is proportional to the ionic strength of the urine. Therefore, by assaying the ionic strength of the test sample, the USG can be determined indirectly and semi-quantitatively by correlating the ionic strength of the urine to the USG.

Conventional reagent strips are usually made in such a way that all the relevant reagents are diffusively immobilized together on a small porous zone on the strip. A sample of urine is then applied to the zone or the entire strip is dipped in the urine sample and then pulled out quickly to allow color to develop. Examples of such conventional reagent strips are described in U.S. Pat. No. 4,318,709 to Falb et al. and U.S. Pat. No. 4,376,827 to Stiso et al.

U.S. Pat. No. 4,318,709 to Falb et al. and U.S. Pat. No. 4,376,827 to Stiso et al., both of which are incorporated by reference herein, describe the polyelectrolyte-dye ion exchange chemistry utilized in conventional test strips for measuring USG. In such conventional test strips, ions present in urine induce an ion-exchange with a polyelectrolyte, thereby introducing hydrogen ions into the urine. The change in hydrogen ion concentration is detected by a pH indicator.

However, conventional reagent strips for USG measurement suffer from major shortcomings, particularly for over-the-counter and point-of-care markets. For instance, conventional reagent strips have a limited reading window because the signal produced by such strips begins to change only a short period of time after sample application. Signal change can be caused by reagent leaching (the result of diffusively immobilized reagents) and sample evaporation. Unless the strips are analyzed shortly after application of the sample, the signal change can lead to erroneous test results. Furthermore, because the reagents in conventional strips are typically water soluble, the strips must also be pulled out quickly from the urine sample to prevent the reagents from leaching into the sample. In addition, conventional reagent strips are often designed for only a single urine sample application. Multiple urine insults can lead to erroneous test results making such strips unsuitable for applications in absorbent articles where multiple urine insults cannot be controlled. Finally, conventional reagent strips do not provide a way for a user to know if the test has been performed correctly or if enough sample has been applied.

Although several kinds of dehydration dipsticks have existed for many decades, the existing technologies cannot meet the requirements for absorbent products. Some manufacturers of health and hygiene products have desired to broaden the appeal of their products to many consumers. These manufactures have a long felt desire to integrate dehydration sensors with absorbent products. This need has spurred development of low cost dehydration sensors that can be integrated into an absorbent article, such as a diaper or an incontinent garment. Nonetheless, previous lateral flow-based dehydration sensors that are feasible for incorporation into absorbent products are relatively complicated and economically inhibitive for integration of the sensors into every kind of absorbent garment. Thus, a need exists for an assay device that can provide such assurance to caregivers in a cost effective way.

SUMMARY OF THE INVENTION

The present invention relates to a membrane-free fluidic assay device or dehydration sensor that can be integrated into an absorbent personal care article. The dehydration sensor employs ion-responsive and charged polymeric surfactants to both immobilize oppositely charged indicators, as well as improve the wettability of the sensors. The charged polymeric surfactants are highly soluble in water but will precipitate when in a buffered or salt solution of high concentration of about 1 wt. % or greater. The amount of charged surfactant can be up to about 22 wt. %. In other words, the polymeric surfactant exhibits decreasing solubility with increasing salt concentration in an aqueous solution.

Unlike conventional lateral flow-based dehydration devices, the polymeric surfactant and pH indicator can be printed or otherwise applied as a coating directly on the active surface of the porous substrate. The need for a separate film or membrane to immobilize the pH indicator, which many conventional lateral flow devices employ, is eliminated. Hence, the present inventive arrangement minimizes or eliminates a physical interface between the film membrane, which conventionally holds the pH indicator, and the underlying porous substrate, which conventionally supports the buffer components. Furthermore, the present invention can reduce the cost and simplify the process of fabricating lateral flow sensors.

The dehydration sensor is formed a first substrate with a porous matrix adapted for conducting lateral flow. The substrate includes a sample contact zone and a detection or indicator zone as part of a buffer pad, a feedback zone as part of a wicking pad situated downstream of the detection zone. The detection zone has a buffering component comprising a weak polymeric acid and weak polymeric base with a pKa $\leq 10^{-3}$ or $10^{-2}$, and a class of charged polymeric surfactants that are responsive to relative ion concentrations in a sample solution, and a charged pH indicator with a charge opposite to that of the charged polymeric surfactant. The charged polymeric surfactant is soluble in amounts of greater than or equal to about 1% by weight ($\geq 1$ wt. % solute) in water and aqueous solutions of low ionic concentration of $\leq 0.1$ wt. % salts, but insoluble ($<1$ wt. % solute) in aqueous solution of high ionic concentrations of $>0.1$ wt. % salts.

The dehydration sensors are much simpler and cheaper to fabricate than prior designs. The present invention moves one step closer to the possibility of integrating a dehydration sensor in every kind of absorbent product. Desirably the dehydration sensor is formed from a single porous substrate. The advantage of a single, integrated substrate is that there will be no interface or edge effects tend to arise in dehydration sensors that use different kinds of materials.

In other embodiments, a feature of the dehydration sensor can regulate or control the sample flow rate and modulate the manifestation of test results to reduce or eliminate errors. The assay device has a first substrate with a porous matrix adapted for conducting lateral flow. The substrate has a sample contact zone, a detection zone, an observation-feedback zone, and a flow-rate control zone situated between the detection zone and feedback zone. Each of the respective zones is in fluidic communication with each other either directly or indirectly. The flow-rate control zone contains a separate, discrete substrate, such as a membrane or film, which can have a different porosity gradient or have a variety of flow-path features or micro-channels that help to regulate the progress of a sample volume from one section of the substrate to another. A supporting member secures each of the zones together in an integrate device.

The detection zone can be part of a buffer pad situated between the sample contact zone and the flow-rate control zone, or alternatively the observation-feedback zone, which is part of a wicking pad. The wicking pad may further include a sample observation-control zone that changes color upon contact with a urine sample, regardless of specific gravity of the urine. The flow-rate control zone regulates the flow rate from the buffer pad to the wicking pad. In some embodiments, the flow-rate control zone can be part of the same substrate as the wicking pad; but in other embodiments, the flow-rate control zone is at least part of a second substrate that separates from the first substrate. The flow-rate control zone has a porous membrane that bridges a gap between the buffer pad and the wicking pad. A variety of flow-rate control devices or mechanism may be arranged between the detection zone and the sample observation-feedback zone, with regions that overlap with the flow-rate control zone, to modulate or regulate the lateral flow of urine or other fluids as the fluid progresses from the deposition zone of the first or inner face to the detection zone of the second or outer face. The flow-rate control zone regulates the amount of time needed for development and appearance of a visual signal in the observation-feedback zone until the color transition in the detection zone reaches color stability. The mechanisms may take the form, for example, of micro-channels arranged in predetermined patterns and/or one or a number of differentiated substrate densities. These mechanisms may be oriented either parallel or orthogonal to the flow path of fluid. The flow-rate control zone regulates a predetermined time before the development of a visual signal in the observation-feedback zone so that color transition in the detection zone reaches color stability.

In another aspect, the present invention also describes a method for quantitatively or semi-quantitatively determining the ionic strength, or specific gravity, of a test sample of urine. The method includes providing a lateral flow device with a porous matrix in fluid communication with a buffer pad or zone and an indicator zone; introducing a test sample to a sample zone on said buffer pad, allowing said sample to seep through a detection zone to said flow-rate control zone before developing a visual signal in an indicator or wicking zone. The buffering zone including a polyelectrolyte disposed therein, the indicator zone including a pH indicator non-diffusively immobilized therein, the indicator zone being separate from the buffering zone and in fluid communication with the buffering zone, the polyelectrolyte capable of an ion-exchange with the ions in the urine so as to add or reduce hydrogen ions into the urine, the pH indicator capable of producing a signal corresponding to the change in the hydrogen ion concentration in the urine. The polyelectrolytes can include partially neutralized weak polymeric acids and bases. The test sample is contacted with the fluidic medium of the lateral flow device to determine the ionic strength of the urine based on the signal produced by the pH indicator.

Alternatively, a method for testing ion strength of a urine sample is provided. The method involves: introducing a urine sample to a testing device such as described above with a sample zone and a detection zone with a weak acid and/or weak base, passing or allowing the urine to migrate through a buffer pad with the detection zone, causing a color change of a pH indicator in said detection zone. In some embodiments one also passes the urine through a the flow-rate control zone to regulate the time needed for appearance of a visual signal in a control-feedback zone of the wicking pad until a color transition in the detection zone attains color stability.

In another aspect, the present invention also relates to an absorbent article incorporating a lateral fluidic assay device as described above, for monitoring hydration or dehydration, and comprising: a first substrate with a porous matrix adapted for conducting lateral flow, the substrate having a sample contact zone, a detection zone, an observation-feedback zone, and a flow-rate control zone situated between the detection zone and the feedback zone, wherein each of the zones is in fluidic communication with each other with directly or indirectly by an adjacent component. The absorbent article would be capable of determining the ionic strength of urine. The article includes a substantially liquid impermeable layer, a liquid permeable layer, an absorbent core positioned between the substantially liquid impermeable layer and the liquid permeable layer, and a lateral flow assay device integrated into the article and positioned such that the device is in fluid communication with the urine when provided by a wearer of the article. Examples of absorbent articles may include, diapers, adult incontinence products, or personal or feminine hygiene products, or absorbent pads for medical or hospital uses.

Alternatively, the invention describes an insert for a garment (e.g., underwear) or absorbent personal care product, the insert comprising an assay apparatus having: a lateral flow strip having a porous matrix in fluid communication with a buffer pad, wicking pad, and a flow-rate control zone situated between said buffer pad and wicking pad, said flow-rate control zone regulates an amount of time needed for development and appearance of a visual signal in a control-feedback zone of said wicking pad until a color transition in a detection zone of said buffer pad attains color stability.

Additional features and advantages of the present three-dimensional sensor or assay device and associated absorbent articles containing such a sensor will be described in the following detailed description. It is understood that the foregoing general description and the following details description and examples are merely representative of the invention, and are intended to provide an overview for understanding the invention as claimed.

DETAILED DESCRIPTION OF THE INVENTION

The present invention builds upon prior generations of lateral flow dehydration test devices, such as described in U.S. patent application Ser. No. 11/956,428, the contents of which are incorporated herein by reference. In particular, present invention provides a dehydration sensor that incorporated an ion-responsive and charged polymeric surfactants.

In another aspect, the invention describes, in part, a test device for quantitatively or semi-quantitatively determining the ionic strength of a test sample of urine is provided. The test device includes a lateral flow-adapted substrate or device comprising a fluidic medium defining a buffering zone and a detection or indicator zone, the buffering zone including a polyelectrolyte disposed therein, the indicator zone includes a pH indicator non-diffusively immobilized therein, the indicator zone being separate from the buffering zone and in fluid communication with the buffering zone, the polyelectrolyte capable of an ion-exchange with the ions in the urine so as to add or reduce hydrogen ions into the urine, the pH indicator capable of producing a signal corresponding to the change in the hydrogen ion concentration in the urine. The polyelectrolytes can include partially neutralized weak polymeric acids and bases. The test sample is contacted with the fluidic medium of the lateral flow device to determine the ionic strength of the urine based on the signal produced by the pH indicator. The lateral flow strip has a porous matrix that permits fluid communication with the buffer pad, wicking pad, and may include a flow-rate control zone situated between the buffer and wicking pads.

Section I

Buffer Ink with Ion-Responsive and Charged Polymeric Surfactants

The present invention can satisfy the need for a better and more stable dehydration sensor. According to the invention, the dehydration sensor is composed of a single, integrated, porous substrate (e.g., a piece of cellulosic pad or filter paper), with a coating of 1) a buffering component made from a partially neutralized weak acid or weak base with a dissociation constant of less than or equal to about $10^{-2}$ (pKa value $\leq 10^{-2}$; desirably $\leq 10^{-3}$), 2) a charged polymeric surfactant, and 3) a pH indicator that has a charge opposite to that of the polymeric surfactant. The buffering component, charged surfactant, and indicator are all deposited on the same surface of the porous substrate. (The charged polymeric surfactant can be adapted from similar materials as described in U.S. Pat. Nos. 7,456,117 B2, 7,157,389 B2, 6,960,371 B2, or 6,828,014 B2, the contents of which are incorporated herein by reference.) The three components may be deposited on the same location together or on different locations of the porous substrate. The coating can be applied either over the entire surface of the substrate or in a limited, localized area of the surface. The coatings can be applied using conventional printing techniques.

The pKa of the weak acid should be less than about $10^{-3}$, which permits the salt content in the urine sample to influence the equilibration between the salt form and acid form. The pKa of the weak base should also be less about than $10^{-3}$, which permits the salt content in the urine to influence the equilibration between the protonated form and the base form. The weak acid or base in the buffer can be, for instance, a weak polymeric acid (e.g., polyacrylic acid), or weak polymeric base (e.g., polyimine). The pH indicator can be a dye or colorant (e.g., bromothymol blue, nitrazine yellow, neutral red), the specific color change of which depending on the pH. An important feature of the invention is the incorporation of an unusual class of polymeric surfactants that are charged and responsive to relative ion concentrations in solution. The charged polymeric surfactant plays a dual role of acting as an immobilization agent and a wettability enhancing agent. The surfactants are soluble in water and aqueous solutions of low ionic concentration, yet insoluble in aqueous solution of high ionic concentrations. The surfactants tend to be soluble, in amounts of greater than or equal to about 1% by weight ($\geq 1$ wt. % solute), in pure water and aqueous solution of low ionic concentration (i.e., $\leq 0.1$ wt. % for salts), yet insoluble (i.e., <1 wt. % solute) in an aqueous solution of high ionic concentrations (i.e., >0.1 wt. % salts). The sensor takes advantage of this unique property as a way to immobilize non-diffusively charged indicators, while at the same time, improving the wettability of the substrate. Ordinary charged surfactants cannot accomplish this feature because those kinds of surfactants are water soluble in a wide range of ionic concentrations. For dehydration sensors where a high concentration of a buffer is needed, immobilization and wettability enhancement by the surfactant can be achieved, which significantly simplifies the fabrication and use of the sensors.

The surfactant can be either cationic or anionic. For example, one may use SSB-6: poly[acrylic acid-co-butyl acrylate-co-2-ethylhexylacrylate-co-sodium-2-acrylamidopropane sulfonate], or OASIS "L7170": Poly[methyl acrylate-co-[2-acryloyloxy) ethyl]trimethyl ammonium chloride]). The amount of charged polymeric surfactant can be from about 0.1 wt. % up to about 20 wt. % or 22 wt. %, but typically is between about 0.5 or 1 wt. % to about 15 or 17 wt. %, more typically between about 1.5 or 3 wt. % to about 10 or 12 wt. %, and desirably between about 2 or 4 wt. % to about 7 or 8 wt. %. Particular embodiments, for example, can have a range from about 1-5 wt. %.

Unlike the previous generation lateral-flow-based dehydration sensors, a lateral-flow dehydration sensor according to the present invention is configured to have all of the reagents deposited on the same, single porous substrate without need for any interface in between the substrate with indicator immobilized thereon and porous substrate with buffer thereon. This structural configuration helps to promote good sample flow and reagent mixing. The inventive dehydration sensor enables one to dispense with the use of an indicator pad and a feedback zone pad, such as commonly employed in other dehydration sensors. Instead of employing charged membranes to immobilize the indicators for the detection zone and feedback zone, the new sensor uses charged polymeric surfactants to immobilize the oppositely charged indicators on a single, integrated, porous substrate with buffer components. Unlike prior generation dehydration sensors that needed to use multiple interfaces, through which the liquid sample has to pass through before completing assay testing, the current sensor does not have any interface that may interfere with the liquid flow. As a result, the present inventive dehydration sensors exhibit better performance in terms of consistency of results over many tests.

Additionally, whereas the previous sensor designs required separate physical parts and needed several steps to assemble the whole sensor device, fabrication of the current sensor is simplified, and can be made by means of two general steps. First, provide a substrate with a porous matrix, either saturate with or deposit a sufficient amount of buffer solution components on to the porous matrix, and allow the buffer-coated substrate to dry. Second, then, apply a pH indicator and charged polymeric surfactant solution to the dried buffer-coated substrate. The pH indicator and charged polymeric surfactant can be printed or otherwise applied to the substrate either together simultaneously or separately in series. When co-deposited, the surface area of the substrate with the pH indicator should overlap with at least a portion of the area that has the charged polymeric surfactant applied, and vice-versa. Further, the reduced materials and complexity of the devices makes them much less expensive to make, which is an advantage for widespread implementation of such sensors in many consumer-use absorbent products.

Examples of porous matrices include cellulose pads, filter papers, non-woven materials and glass fibers pads. A method for quantitatively or semi-quantitatively determining the ionic strength of a test sample of urine, the method comprises: providing a lateral flow assay device having a porous medium defining a buffering zone and a detection or indicator zone. The porous matrix should not interfere significantly with the association and dissociation constant of the buffer. The dehydration test device has a test pad (zone) that non-diffusively immobilizes with a pH indicator. The pH indicator desirably exhibits a color transition around neutral pH, or at a pH from about 5.5 to about 10.5. Examples of the pH indicator include bromothymol blue, thymol blue, m-cresol purple, brilliant yellow and neutral red. The matrix is preferred to be porous and urine (aqueous) friendly to allow rapid penetration of urine.

The buffering zone including a polyelectrolyte disposed therein, the detection zone having a buffering component comprising a weak polymeric acid and weak polymeric base with a pKa $\leq 10^{-2}$, and a class of charged polymeric surfactants that are responsive to relative ion concentrations in a sample solution, and a charged pH indicator with a charge opposite to that of the charged polymeric surfactant, non-diffusively immobilized therein. The buffer may consist of partially neutralized weak polymeric acid or base. Examples of the weak polymeric acids or bases may include poly (acrylic acid), poly(maleic acid), poly(vinylamine) and poly (4-vinylpyridine). The buffer may consist of non-polymeric weak acids such as 2-(N-morpholino)-ethanesulfonic acid and bis-(aminoethyl)-glycol ether N,N,N',N'-tetraacetic acid.

The dehydration sensor can be made by several simple methods. One example of making a dipstick dehydration sensor involves: applying a buffering solution of partially neutralized weak acids or bases (e.g., polymeric bases is deposited onto a porous substrate, such as a piece of cellulose pad or a piece of filter paper, and then drying the porous substrate. Typically, the buffering solution is an aqueous solution. An indicator solution that contains one or more ion-responsive charged polymeric surfactants and one or more pH indicators are deposited together on the porous substrate and dried to make the final dipstick sensors. The indicator solution can be a solution containing water, volatile organic solvents or both. The amount of the charged polymeric surfactant is at least twice as much as the charged pH indicator in weight percent. Alternatively, another example of fabricating a dipstick dehydration sensor involves: providing a buffer solution containing partially neutralized weak acids or bases and one or more ion-responsive charged polymeric surfactants and depositing the buffer solution on an integrated, single, porous substrate and drying the porous substrate. An indicator solution that contains one or more pH indicators is deposited on the porous substrate and dried to make the final dipstick sensors. The indicator solution can be a solution containing water, volatile organic solvents, or both.

Several ways can be employed to make a lateral flow format dehydration sensor according to the present invention. According to an embodiment of the invention, one way, for instance, is to first, provide a strip of porous substrate such as cellulose pads or filter papers, and to soaked the substrate with a solution containing partially neutralized weak acids or bases and one or more ion-responsive charged polymeric surfactants and is dried. Then, an indicator solution containing one or more charged pH indicators for detection zone and/or an indicator for feedback zone are either simultaneously or separately striped on the different positions of the porous substrate and the porous strip is then dried to make the lateral flow dehydration sensor. Later, the sensor may be further sealed in a detection and feedback zone to minimize the evaporation of a sample.

The present invention helps to bind indicator molecules stably to the surface of the substrate and prevent them from leaching from the designated testing or observation sites on the sensor. According to an embodiment, the sensor can take the form of a dipstick, but unlike conventional dipsticks for dehydration detection, the indicator on the sensor will not leach from the substrate.

According to another example, a buffering solution of partially neutralized weak acids or bases is first deposited on a porous substrate and the porous substrate is then dried. An immobilization solution that contains the ion-responsive charged polymeric surfactants is deposited subsequently on the porous substrate and the substrate is again dried. Finally, an indicator solution of the charged pH indicators is deposited on the porous substrate and the substrate is dried. The substrate can be scored and cut into appropriately sized strips to make the final dipstick sensors.

In a further embodiment, unlike conventional dipsticks that have only a detection zone, the inventive dipstick dehydration sensor can be configured to have both a detection zone and a feedback zone. An advantage of having both of these zones together on a single substrate is that it enables the user to know whether the device has performed properly and the signal on the device has developed properly, or communicates whether sufficient amount of urine sample has been applied to the device. The pH indicator in the detection zone exhibits either different colors or intensities of color or hues in response to the ion strength of a sample of analyte. The indicator in the feedback zone will show a color change once the sample is in contact with the sensor no matter what its ion strength. The simple permanent immobilization of the ion-response charged polymeric surfactant makes this possible.

When fabricating the sensor, for example, one can deposit a buffering solution of partially neutralized weak acids or bases on a porous substrate and the porous substrate is dried. Then, an immobilization solution that contains the ion-responsive charged polymeric surfactants is deposited on the porous substrate and the substrate is dried. A pH indicator solution of the charged pH indicators is then deposited on a first predetermined location of the porous substrate for a detection zone and another charged indicator solution is deposited on a second predetermined location of the porous substrate to make a feedback zone. The two predetermined locations are separate, distinct and/or remote from each other. The substrate is allowed to dry before making the final sensors.

Section II

Dehydration Monitoring Lateral Flow Format

Conventional urine testing devices, such as dipsticks or test strips, operate by dipping the dipstick in a urine sample and pulling it out quickly, and then read the resultant color that can be compared with a color scale. Typically these test strips have a short reading window, typically about or less than two minutes, and do not have any user feedback mechanism. Unlike previously developed lateral flow hydration test formats, the hydration monitoring and assay device according to U.S. patent application Ser. No. 11/956,428, has a reading window with a much longer duration of at least about 2 hours, typically about 4-6 hours or greater, with stable color signal and a user feedback zone to indicate a sample volume and sample contact with the test zone. The long reading window and long term stability of the color signal and user feedback mechanism are important features for an over-the-counter (OTC) test format, in particular, for a test in a personal care product, where constant monitoring is not practical.

No external dehydration sensing technologies currently available can provide a feasible solution to consumer-use absorbent products. Previous generation dehydration sensors based on a lateral flow format can be integrated into an absorbent product by providing a stable signal and a feedback mechanism. While that kind of sensor is relatively inexpensive to fabricate (less than about 5 cents per device) and is feasible to put in an absorbent product such as an insert on a needed basis, the cost is still too high for general use with every kind of consumer personal-care absorbent product. In order to reduce the cost of the sensor, a dehydration sensor that is much simpler and cheaper to make is needed. One can achieve such a sensor by means of a new immobilization and wetting technique.

The present invention provide an improved lateral flow assay device and format for monitoring specific gravity of urine. The present invention builds upon and advances beyond the development of prior hydration sensors, such as described in U.S. Patent Application Publication No. 2009/0157024, the content of which, in its entirety, is incorporated herein by reference.

Urine specific gravity (USG) can be utilized to indicate the presence or degree of dehydration in human subjects. Since the specific gravity of urine is correlated to the ionic strength of urine, measurements of urine ionic strength can be used to estimate specific gravity in devices screening for the presence or severity of dehydration.

In that regard, the present disclosure is generally directed to a lateral flow assay device for determining the ionic strength of urine. The device can include a buffering zone with a polyelectrolyte disposed therein and an indicator zone with a pH indicator non-diffusively immobilized therein.

Non-diffusive immobilization of the pH indicator can greatly extend the period of time that the signal for ionic strength remains stable. In addition, the physical separation of certain of the reagents can reduce the impact of any sample loss or diffusion over time on pH fluctuation around the pH indicator.

In certain embodiments, casing material can cover at least a portion of the buffering zone and a portion of the indicator zone so as to prevent exposure of such covered portions to the outside environment. Casing material can minimize sample evaporation and can also limit reagent exposure to users of the test device. Additionally, in certain embodiments, a control zone can also be present to provide users with an indication that the test has been performed correctly.

The devices described herein provide a simple, user-friendly, cost-effective approach for rapid measurement of hydration status through urine. Additionally, the devices described herein can be incorporated into absorbent articles such as diapers and incontinent pads to assist in determining USG.

Figure 1:
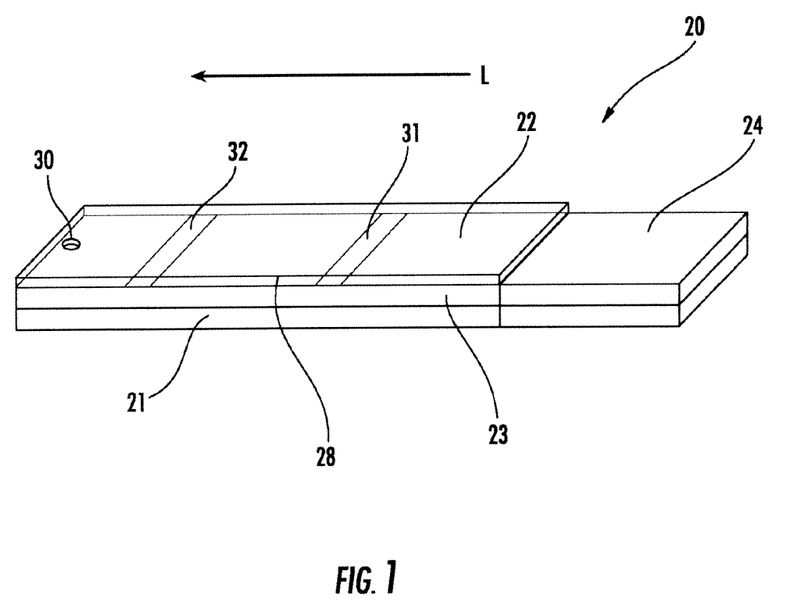
FIG. 1 is a three-quarter schematic representation of a lateral flow assay device according to the present invention.

Referring to FIG. 1, one embodiment of a lateral flow device 20 that can be formed according to the present disclosure will now be described in more detail. As shown, the device 20 contains a chromatographic medium 23 optionally supported by a rigid support material 21. In general, the chromatographic medium 23 can be made from any of a variety of materials through which the urine is capable of passing. For example, the chromatographic medium 23 can be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium 23 is formed from a Biodyne® Plus membrane made by Pall Corporation.

The size and shape of the chromatographic medium 23 can generally vary as is readily recognized by those skilled in the art. For instance, a porous membrane strip can have a length of from about 10 to about 100 millimeters, in some embodiments from about 20 to about 80 millimeters, and in some embodiments, from about 40 to about 60 millimeters. The width of the membrane strip can also range from about 0.5 to about 20 millimeters, in some embodiments from about 1 to about 15 millimeters, and in some embodiments, from about 2 to about 10 millimeters. The thickness of the membrane strip can be less than about 500 micrometers, in some embodiments less than about 250 micrometers, and in some embodiments, less than about 150 micrometers.

As stated above, the support 21 carries the chromatographic medium 23. For example, the support 21 can be positioned directly adjacent to the chromatographic medium 23 as shown in FIG. 1, or one or more intervening layers can be positioned between the chromatographic medium 23 and the support 21. Regardless, the support 21 can generally be formed from any material able to carry the chromatographic medium 23. Also, it is generally desired that the support 21 is liquid-impermeable so that fluid flowing through the medium 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the chromatographic medium 23, the support 21 is generally selected to have a certain minimum thickness. Thus, for example, the support 21 can have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers can be obtained from Millipore Corp. of Bedford, Mass. under the name "SHF180UB25."

As is well known the art, the chromatographic medium 23 can be cast onto the support 21, wherein the resulting laminate can be die-cut to the desired size and shape. Alternatively, the chromatographic medium 23 can simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

To initiate the measurement of the ionic strength of urine, a user can directly apply the test sample to a portion of the chromatographic medium 23 through which it can then travel in the direction illustrated by arrow "L" in FIG. 1. Alternatively, the test sample can first be applied to a sample application zone 24 that is in fluid communication with the chromatographic medium 23. As shown in FIG. 1, the sample application zone 24 can be formed on the medium 23. Alternatively, the sample application zone 24 can be formed by a separate material, such as a pad. Some suitable materials that can be used to form such sample pads include, but are not limited to, nitrocellulose, cellulose, porous polyethylene pads, and glass fiber filter paper. If desired, the sample application zone 24 can also contain one or more pretreatment reagents, either diffusively or non-diffusively attached thereto.

In the illustrated embodiment, the test sample travels from the sample application zone 24 to a buffering zone 22 that is in communication with the sample application zone 24. As shown in FIG. 1, the buffering zone 22 can be formed on the medium 23. Alternatively, the buffering zone 22 is formed by a separate material or pad. Such a buffering pad can be formed from any material through which the test sample is capable of passing, such as glass fibers or other such materials already described herein. It should also be understood that the sample application zone 24 can be defined as part of the buffering zone 22.

To facilitate measurement of the ionic strength of urine in the manner described above, a polyelectrolyte at a certain pH is disposed in the buffering zone 22. In some embodiments, the polyelectrolyte can be diffusively immobilized in the buffering zone 22 of the device 20 prior to application of the test sample. The polyelectrolyte can be disposed downstream from the sample application zone 24. In this manner, the urine sample is capable of mixing with the polyelectrolyte upon application. Alternatively, the polyelectrolyte can be positioned upstream from the sample application zone 24. For instance, a diluent can be employed to induce mixing between the polyelectrolyte and test sample. In this manner, the urine sample is capable of mixing with the polyelectrolyte upon application.

As described above, ions present in urine induce an ion-exchange with the polyelectrolyte, thereby adding or reducing hydrogen ions in the urine. In this regard, a suitable polyelectrolyte can include a polymeric acid or a polymeric base, particularly weak polymeric acids and weak polymeric bases. Weak polymeric acids or bases change their apparent association/dissociation constants with the change of ion strength of their environments. For instance, when cation concentration increases, the dissociation constant of a carboxylic acid-based weak acid increases to release more protons to increase the acidity of the solution.

The selection of buffer components can be important for the measurement sensitivity and color change threshold of the device. In certain embodiments, the buffer system is preferably a partially neutralized weak polymeric acids or a partially neutralized weak polymeric base. In this regard, the apparent association constants or dissociation constants of the acids or bases utilized should be sufficiently sensitive to ion strength. There are a number suitable weak polymeric acids and bases that can be utilized with the present disclosure. For example, useful weak polymeric acids can include poly(acrylic acid), poly(maleic acid), maleic acid vinyl methyl ether copolymer, poly(methacrylic acid), styrenemaleic acid copolymer, and maleic anhydride/methylvinylether copolymer. Useful weak polymeric bases can include poly(vinylamine) and poly(4-vinylpyridine). However, it should be understood that any suitable polyelectrolyte is contemplated by the present disclosure.

In certain embodiments, polymeric acids or bases can be neutralized at least 50% to make an effective sensitive buffer. The initial pH of the buffer can normally be adjusted to a certain range so that the threshold color changes of the specific gravity can be tailored to some degree. For example, the threshold detection of USG is slightly higher when the initial buffer pH is higher and when a partially neutralized weak polymeric acid is used. However, the adjustments can be limited by the intrinsic association/dissociation constants of the acids or bases utilized. The threshold of color transition can also be adjusted by using different buffer components.

For instance, a significant color change occurs around 1.020 of USG for poly(vinyl chloride-co-vinyl acetate-co-maleic acid while the threshold transition point is around 1.010 for poly(acrylic acid) when both buffers have the initial pH of 7.95.

Referring again to FIG. 1, the lateral flow device 20 includes an indicator zone 31 within which a pH indicator is non-diffusively immobilized. The indicator zone 31 is separate from the buffering zone 22 but positioned adjacent to and in fluid communication with the buffering zone 22. Alternatively, the indicator zone 31 can be formed by a separate material, such as a pad. Some suitable materials that can be used to form such sample pads include, but are not limited to, nitrocellulose, cellulose, porous polyethylene pads, and glass fiber filter paper. In this regard, the indicator zone 31 is still positioned adjacent to and in fluid communication with the buffering zone 22.

The pH indicator can be applied directly to the medium 23 or first formed into a solution prior to application. Various solvents can be utilized to form the solution, such as, but not limited to, acetonitrile, dimethylsulfoxide (DMSO), ethyl alcohol, dimethylformamide (DMF), and other polar organic solvents. The amount of the pH indicator in the solution can range from about 0.001 to about 100 milligrams per milliliter of solvent, and in some embodiments, from about 0.1 to about 10 milligrams per milliliter of solvent. In one particular embodiment, the indicator zone 31 is defined by the chromatographic medium 23 and formed by coating a solution thereon using well-known techniques and then dried. The pH indicator concentration can be selectively controlled to provide the desired level of detection sensitivity.

It is desired that the pH indicator be applied in a manner so that it does not substantially diffuse through the matrix of the chromatographic medium 23 (i.e., non-diffusively immobilized). This enables a user to readily detect the change in color that occurs upon reaction of the pH indicator with the urine and also prevents the pH indicator from leaching out of the indicator zone 31. The immobilization can be achieved by many methods such as chemical bonding, physical absorption, or using a carrier such as a polymer or a particle. In one preferred embodiment, a highly charged porous material can effectively immobilize an oppositely charged indicator. In this regard, useful charged porous substrates can include nylon membranes such as Biodyne®. Plus from Pall Corporation. Porous non-woven materials such as paper tissues treated with Kymene® have also been found to be suitable charged materials to immobilize negatively charged indicators.

In certain embodiments of the present disclosure, a crosslinked network containing the pH indicator is formed on a chromatographic medium of a lateral flow device. Without intending to be limited by theory, it is believed that the crosslinked network can help durably secure the pH indicator, thereby allowing a user to more readily detect a change in its color during use. The crosslinked network can contain "intra-cross links" (i.e., covalent bonds between functional groups of a single molecule) and/or "inter-cross links" (i.e., covalent bonds between different molecules, e.g., between two pH indicator molecules or between a pH indicator molecule and the substrate surface). Crosslinking can be carried out via self crosslinking of the indicator and/or through the inclusion of a separate crosslinking agent. Suitable crosslinking agents, for instance, can include polyglycidyl ethers, such as ethylene glycol diglycidyl ether and polyethylene glycol dicglycidyl ether; acrylamides; compounds containing one or more hydrolyzable groups, such as alkoxy groups (e.g., methoxy, ethoxy and propoxy); alkoxyalkoxy groups (e.g., methoxyethoxy, ethoxyethoxy and methoxypropoxy); acyloxy groups (e.g., acetoxy and octanoyloxy); ketoxime groups (e.g., dimethylketoxime, methylketoxime and methylethylketoxime); alkenyloxy groups (e.g., vinyloxy, isopropenyloxy, and 1-ethyl-2-methylvinyloxy); amino groups (e.g., dimethylamino, diethylamino and butylamino); aminoxy groups (e.g., dimethylaminoxy and diethylaminoxy); and amide groups (e.g., N-methylacetamide and N-ethylacetamide).

Any of a variety of different crosslinking mechanisms can be employed in the present disclosure, such as thermal initiation (e.g., condensation reactions, addition reactions, etc.), electromagnetic radiation, and so forth. Some suitable examples of electromagnetic radiation that can be used in the present disclosure include, but are not limited to, electron beam radiation, natural and artificial radio isotopes (e.g., .alpha., .beta., and .gamma. rays), x-rays, neutron beams, positively-charged beams, laser beams, ultraviolet, etc. Electron beam radiation, for instance, involves the production of accelerated electrons by an electron beam device. Electron beam devices are generally well known in the art. For instance, in one embodiment, an electron beam device can be used that is available from Energy Sciences, Inc., of Woburn, Mass. under the name "Microbeam LV." Other examples of suitable electron beam devices are described in U.S. Pat. No. 5,003,178 to Livesay; U.S. Pat. No. 5,962,995 to Avnery; U.S. Pat. No. 6,407,492 to Avnery, et al., which are incorporated herein in their entirety by reference thereto for all purposes. The wavelength .lamda. of the radiation can vary for different types of radiation of the electromagnetic radiation spectrum, such as from about 10.sup.-14 meters to about 10.sup.-5 meters. Electron beam radiation, for instance, has a wavelength .lamda. of from about 10.sup.-13 meters to about 10.sup.-9 meters. Besides selecting the particular wavelength .lamda. of the electromagnetic radiation, other parameters can also be selected to control the degree of crosslinking For example, the dosage can range from about 0.1 megarads (Mrads) to about 10 Mrads, and in some embodiments, from about 1 Mrads to about 5 Mrads.

The source of electromagnetic radiation can be any radiation source known to those of ordinary skill in the art. For example, an excimer lamp or a mercury lamp with a D-bulb can be used. Other specialty-doped lamps that emit radiation at a fairly narrow emission peak can be used with photoinitiators which have an equivalent absorption maximum. For example, the V-bulb, available from Fusion Systems, is another suitable lamp for use. In addition, specialty lamps having a specific emission band can be manufactured for use with one or more specific photoinitiators.

Initiators can be employed in some embodiments that enhance the functionality of the selected crosslinking technique. Thermal initiators, for instance, can be employed in certain embodiments, such as azo, peroxide, persulfate, and redox initiators. Representative examples of suitable thermal initiators include azo initiators such as 2,2'-azobis(2,4-dimethylvaleronitrile), 2,2'-azobis(isobutyronitrile), 2,2'-azobis-2-methylbutyronitrile, 1,1'-azobis(1-cyclohexanecarbonitrile), 2,2'-azobis(methyl isobutyrate), 2,2'-azobis(2-amidinopropane) dihydrochloride, and 2,2'-azobis(4-methoxy-2,4-dimethylvaleronitrile); peroxide initiators such as benzoyl peroxide, acetyl peroxide, lauroyl peroxide, decanoyl peroxide, dicetyl peroxydicarbonate, di(4-t-butylcyclohexyl) peroxydicarbonate, di(2-ethylhexyl) peroxydicarbonate, t-butylperoxypivalate, t-butylperoxy-2-ethylhexanoate, and dicumyl peroxide; persulfate initiators such as potassium persulfate, sodium persulfate, and ammonium persulfate; redox (oxidation-reduction) initiators such as combinations of the above persulfate initiators with reducing agents such as sodium metabisulfite and sodium bisulfite, systems based on organic peroxides and tertiary amines, and systems based on organic hydroperoxides and transition metals; other initiators such as pinacols; and the like (and mixtures thereof). Azo compounds and peroxides are generally preferred. Photoinitiators can likewise be employed, such as substituted acetophenones, such as benzyl dimethyl ketal and 1-hydroxycyclohexyl phenyl ketone; substituted alpha-ketols, such as 2-methyl-2-hydroxypropiophenone; benzoin ethers, such as benzoin methyl ether and benzoin isopropyl ether; substituted benzoin ethers, such as anisoin methyl ether; aromatic sulfonyl chlorides; photoactive oximes; and so forth (and mixtures thereof). Other suitable photoinitiators can be described in U.S. Pat. No. 6,486,227 to Nohr, et al. and U.S. Pat. No. 6,780,896 to MacDonald, et al., both of which are incorporated herein by reference.

Although not required, additional components can also be employed within the crosslinked network to facilitate the securement of the pH indicator. For example, an anchoring compound can be employed that links the pH indicator to the surface of the chromatographic medium and further improves the durability of the pH indicator on the lateral flow device. Typically, the anchoring compound is larger in size than the pH indicator, which improves its likelihood of remaining on the surface of the chromatographic medium during use. For example, the anchoring compound can include a macromolecular compound, such as a polymer, oligomer, dendrimer, particle, etc. Polymeric anchoring compounds can be natural, synthetic, or combinations thereof. Examples of natural polymeric anchoring compounds include, for instance, polypeptides, proteins, DNA/RNA and polysaccharides (e.g., glucose-based polymers). Examples of synthetic polymeric anchoring compounds include, for instance, polyacrylic acid and polyvinyl alcohols. One particular example of a polysaccharide anchoring compound is activated dextran. In some embodiments, the anchoring compound can be a particle (sometimes referred to as a "bead" or "microbead"). Naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., can be used. Further, synthetic particles can also be utilized. For example, in one embodiment, latex microparticles are utilized. Although any synthetic particle can be used, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles can generally vary. In one particular embodiment, for instance, the particles are spherical in shape. However, it should be understood that other shapes are also contemplated such as plates, rods, discs, bars, tubes, irregular shapes, etc. In addition, the size of the particles can also vary. For instance, the average size (e.g., diameter) of the particles can range from about 0.1 nanometers to about 1,000 microns, in some embodiments, from about 0.1 nanometers to about 100 microns, and in some embodiments, from about 1 nanometer to about 10 microns.

The manner in which the anchoring compound is used to link the pH indicator and the chromatographic medium can vary. In one embodiment, for instance, the anchoring compound is attached to the pH indicator prior to application of both to the chromatographic medium. In other embodiments, the anchoring compound can be bonded to the chromatographic medium prior to application of the pH indicator. In still other embodiments, the materials can be applied as separate components to the chromatographic medium and attachment reactions can take place in situ, optionally at the same time as the crosslinking of the network. For instance, the pH indicator can bind the anchoring compound, the anchoring compound can bind the medium, and simultaneously, cross-linking reactions can take place between anchoring compounds, between indicators, or between the two. In one such embodiment, the cross-linked network thus formed can be physically held on the porous membrane of the chromatographic medium without the need for bonding between the porous membrane and the other components of the system. In particular, the crosslinked network, portions of which can extend within and among the pores of the porous membrane, can be physically constrained on the membrane, even without specific bonds forming between the membrane and the components of the crosslinked network.

In the case of bonds being formed between the system components, attachment of the anchoring compound to a chromatographic medium as well as attachment of the anchoring compound to the indicator can be accomplished using carboxylic, amino, aldehyde, bromoacetyl, iodoacetyl, thiol, epoxy or other reactive functional groups, as well as residual free radicals and radical cations, through which a binding reaction can be accomplished and according to any suitable methods, e.g., thermal processes, photo-initiated processes, catalyzed reactions, and the like. For example, a chromatographic medium can be amine-functionalized through contact with an amine-containing compound, such as 3-aminopropyltriethoxy silane, to increase the amine functionality of the surface and bind the anchoring compound to the surface via, e.g., aldehyde functionality of the anchoring compound. A surface functional group can also be incorporated on a particle-type anchoring compound as a reactive functionality, for instance when the surface of the particle contains a relatively high surface concentration of polar groups. In certain cases, the particle can be capable of direct bonding to a chromatographic medium and/or a pH indicator without the need for further modification.

It should be understood that, besides covalent bonding, other attachment techniques, such as charge-charge interactions, can also be utilized for attaching the anchoring compound to the chromatographic medium and/or for attaching the pH indicator to the anchoring compound. For instance, a charged anchoring compound, such as a positively charged polyelectrolyte anchoring compound, can be immobilized on a negatively charged chromatographic medium, such as negatively charged porous nitrocellulose membrane, through charge-charge interactions between the two. Similarly, a negatively charged indicator, such as a diazonium ion, can be immobilized on a positively charged anchoring compound.

It is important to select a pH indicator that has sensitivity towards the subtle pH change of the buffer caused by the ion strength of the urine. Since normal urine pH lies around neutral, the indicator is preferred to have a significant color transition around neutral pH of 7.

For instance, in certain embodiments, phthalein chromogens constitute one class of suitable pH-sensitive chromogens that can be employed in the array of the present disclosure. Phenol Red (i.e., phenolsulfonephthalein), for example, exhibits a transition from yellow to red over the pH range 6.6 to 8.0. Above a pH of about 8.1, Phenol Red turns a bright pink (fuschia) color. Derivatives of Phenol Red can also be suitable for use in the present disclosure, such as those substituted with chloro, bromo, methyl, sodium carboxylate, carboxylic acid, hydroxyl and amine functional groups. Exemplary substituted Phenol Red compounds include, for instance, Metacresol Purple (meta-cresolsulfonephthalein), Cresol Red (ortho-cresolsulfonephthalein), Pyrocatecol Violet (pyrocatecolsulfonephthalein), Chlorophenol Red (3',3"-dichlorophenolsulfonephthalein), Xylenol Blue (the sodium salt of para-xylenolsulfonephthalein), Xylenol Orange, Mordant Blue 3 (C.I. 43820), 3,4,5,6-tetrabromophenolsulfonephthalein, Bromoxylenol Blue, Bromophenol Blue (3',3", 5',5"-tetrabromophenolsulfonephthalein), Bromochlorophenol Blue (the sodium salt of dibromo-5',5"-dichlorophenolsulfonephthalein), Bromocresol Purple (5', 5"-dibromo-ortho-cresolsulfonephthalein), Bromocresol Green (3',3",5',5"-tetrabromo-ortho-cresolsulfonephthalein), and so forth. Still other suitable phthalein chromogens are well known in the art, and can include Bromothymol Blue, Thymol Blue, Bromocresol Purple, thymolphthalein, and phenolphthalein (a common component of universal indicators). For example, Bromothymol Blue exhibits a transition from yellow to blue over a pH range of about 6.0 to 7.6; thymolphthalein exhibits a transition from colorless to blue over a pH range of about 9.4 to 10.6; phenolphthalein exhibits a transition from colorless to pink over a pH range of about 8.2 to 10.0; Thymol Blue exhibits a first transition from red to yellow over a pH range of about 1.2 to 2.8 and a second transition from yellow to pH over a pH range of 8.0 to 9.6; Bromophenol Blue exhibits a transition from yellow to violet over a pH range of about 3.0 to 4.6; Bromocresol Green exhibits a transition from yellow to blue over a pH range of about 3.8 to 5.4; and Bromocresol Purple exhibits a transition from yellow to violet over a pH of about 5.2 to 6.8.

A flow-rate control zone that regulates the flow rate of the sample between the buffer pad and wicking pad can also be incorporated. The flow-rate control zone is capable of regulating the period of time that the sample is in a full contact with a detection zone of the buffer pad, and allows the assay reaction to reach a stable signal before the development and appearance of a visual signal in a control-feedback zone of the wicking pad. The detection zone can use a pH indicator that exhibits a color change responding to different pH levels. The sample observation-feedback zone has a non-diffusively immobilized pH indicator and pH adjuster. The pH indicator exhibits a color transition upon contact with the urine sample. The flow-rate control zone has a porosity gradient differential relative to the adjacent buffer pad or the wicking pad. The flow-rate control zone can be fabricated from a variety of materials, such as a nitrocellulose membrane, fiberglass pad, nylon membrane, cellulose pad, filter paper, nonwoven material, or polymeric film.

In certain embodiments, the initial color of the immobilized indicator can be easily adjusted by immobilizing the indicator along with a pH adjuster, either an acid, a buffer, a base or some combination thereof. The initial color is important to provide a sharp color contrast as large as possible. For instance, when bromothymol blue is used as an indicator, basic condition gives the indicator zone a vivid green color, which is clearly distinguishable from yellow color under slightly acidic condition.

Another zone that can be employed in the lateral flow device 20 for improving detection accuracy is a control zone 32. The control zone 32 gives a signal to the user that the test is performing properly. A color forming control is developed on the device downstream from indicator zone. In certain embodiments, a control indicator is immobilized in the control zone along with a pH adjuster to result in an initial pH outside the range of typical pH for a urine sample. In certain embodiments, such a range can include <5.5 or >9.5. The control indicator produces an initial color under the initial pH. Once the urine sample passes through the indicator zone and migrates into the control zone, the pH in the control zone changes to induce a color change for the control indicator, signaling that enough sample has passed through the indicator zone into the control zone and that the test has been done correctly.

Suitable control indicators that can be utilized in the control zone 32 include the pH indicators described previously herein. Additionally, other suitable pH adjusters can include sulfonic acids (e.g., 2-[N-morpholino]ethane sulfonic acid ("MES"), carboxylic acids, and polymeric acids. Specific examples of suitable carboxylic acids are citric acid, glycolic acid, lactic acid, acetic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, carboxymethyl cellulose, and alginic acid. Again, the pH adjuster results in an initial pH outside the range of typical pH for urine (either <5.5 or >9.5) whereby the control indicator produces a signal.

The location of the control zone 32 can vary based on the nature of the test being performed. In the illustrated embodiment, for example, the control zone 32 is defined by the chromatographic medium 23 and positioned downstream from the indicator zone 31. Alternatively, the control zone 32 can be formed by a separate material, such as a pad as described herein with respect to the buffer zone and the detection or indicator zone.

Regardless of the particular control technique selected, the application of a sufficient volume of urine to the device 20 will cause a signal to form within the control zone 32, regardless of the USG. Among the benefits provided by such a control zone is that the user is informed that a sufficient volume of test sample has been added without requiring careful measurement or calculation. This provides the ability to use the lateral flow device 20 without the need for externally controlling the reaction time, test sample volume, etc.

The indicator zone 31 and control zone 32 can generally provide any number of distinct detection regions so that a user can better determine the ionic strength of urine. Each region can contain the same or different materials. For example, the zones can include two or more distinct regions (e.g., lines, dots, etc.). The regions can be disposed in the form of lines in a direction that is substantially perpendicular to the flow of the test sample through the device 20. Likewise, in some embodiments, the regions can be disposed in the form of lines in a direction that is substantially parallel to the flow of the test sample through the device 20.

In addition, portions of one or more zones of the device described herein can be covered by a casing material 28 that limits the exposure of such zone(s) to the outside environment. For instance, a urine sample can evaporate if left in air or some other environment for too great a period of time. The resulting urine can be more concentrated and can lead to inaccurate results. Thus, the present inventor has discovered a technique for reducing this problem by covering the zone(s) to limit the exposure to the outside environment. For instance, referring to FIG. 1, such a casing material 28 that covers the zone(s) can define an opening 30 to allow air to pass out of the device as the urine travels into the device, displacing the air. The opening 30 can be of sufficient size and dimension as would be known in the art to permit a sufficient amount of air to pass out of the device. In certain embodiments, tape can be utilized as the casing material. The casing material can also be utilized to hold the device together. Additionally, the casing material can prevent reagent from leaking out of the device or coming into contact with a user.

In certain embodiments, devices made in accordance with the present disclosure are able to maintain signal strength for at least about 2 hours, more particularly at least about 4 hours, more particularly at least about 6 hours, more particularly at least about 8 hours.

An embodiment of a method for detecting the ionic strength of urine using the device 20 of FIG. 1 will now be described in more detail. Initially, a urine test sample is applied to the sample application zone 24 and travels in the direction "L" to the buffering zone 22. At the buffering zone 22, the ions present in the urine sample induce an ion-exchange with the polyelectrolyte, thereby increasing or decreasing the hydrogen ion concentration in the urine. As the mixture flows through the device 20, the urine and hydrogen ions flow to the indicator zone 31 where the change in hydrogen ion concentration is detected by a pH indicator. Thus, the color or color intensity of the indicator zone 31 can be determined, either visually or with instrumentation. If desired, the intensity of the color at the indicator zone 31 can be measured to quantitatively or semi-quantitatively determine the ionic strength of the urine and, in turn, the USG.

The present disclosure provides a relatively simple, compact and cost-efficient device for accurately detecting USG. The test result can be visible so that it is readily observed by the person performing the test in a prompt manner and under test conditions conducive to highly reliable and consistent test results.

Section III

Absorbent Articles

In accordance with the present disclosure, one or more devices described herein can also be integrated into an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins, swim wear, baby wipes, and so forth; medical absorbent articles, such as garments, fenestration materials, underzones, bedzones, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

Figure 2:
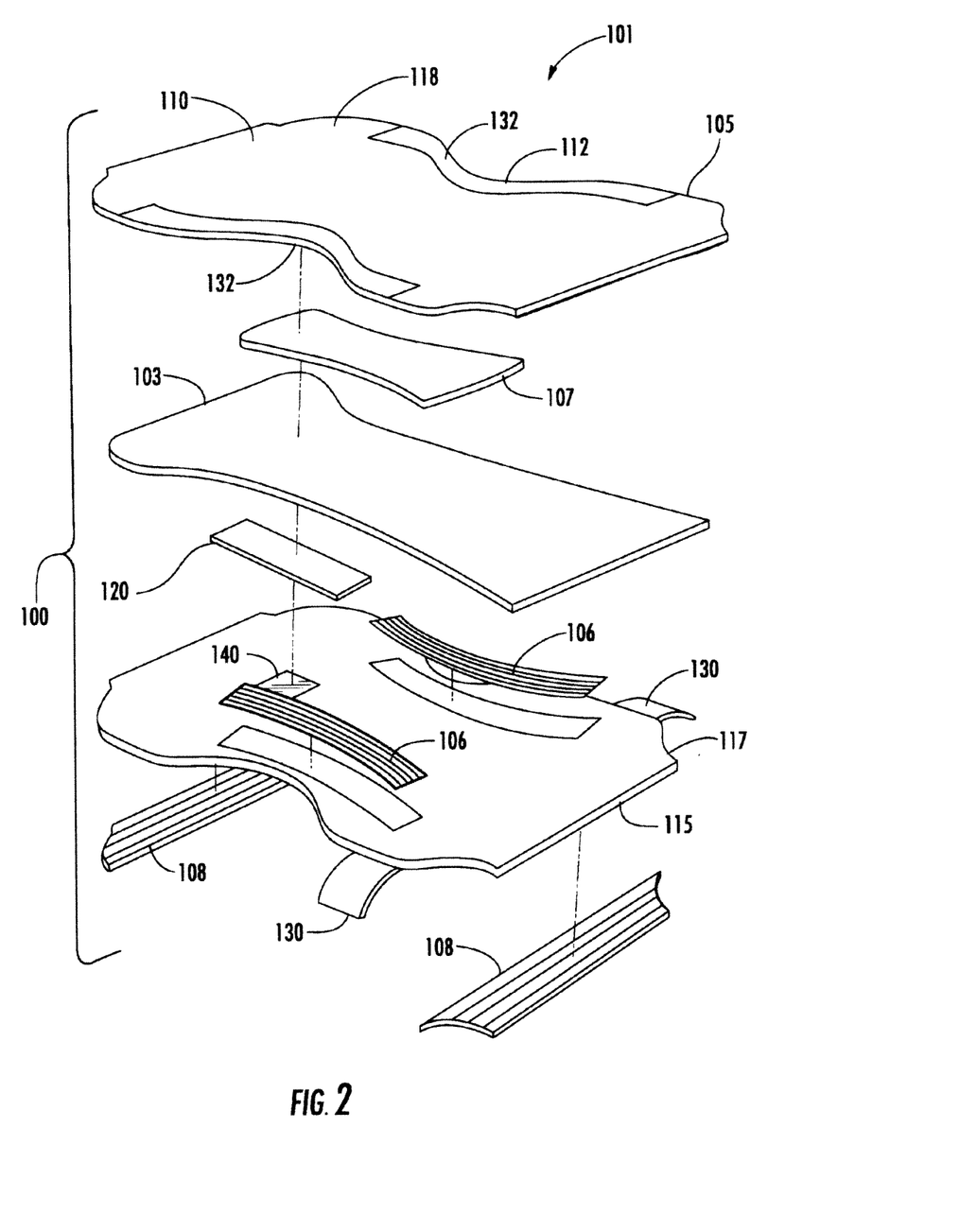
FIG. 2 is a perspective view of an embodiment of an absorbent article according to the present disclosure.

Various embodiments of an absorbent article that can be formed according to the present disclosure will now be described in more detail. For purposes of illustration only, an absorbent article is shown in FIG. 2 as a diaper 101. In the illustrated embodiment, the diaper 101 is shown as having an hourglass shape in an unfastened configuration. However, other shapes can of course be utilized, such as a generally rectangular shape, T-shape, or I-shape. As shown, the diaper 101 includes a chassis formed by various components, including an outer cover 117, bodyside liner 105, absorbent core 103, and surge layer 107. It should be understood, however, that other layers can also be used in exemplary embodiments of the present disclosure. Likewise, one or more of the layers referred to in FIG. 2 can also be eliminated in certain exemplary embodiments of the present disclosure.

The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. As indicated above, the liner 105 can be liquid-permeable to permit liquid to readily penetrate through its thickness. Exemplary liner constructions that contain a nonwoven web are described in U.S. Pat. No. 5,192,606 to Proxmire, et al.; U.S. Pat. No. 5,702,377 to Collier, IV, et al.; U.S. Pat. No. 5,931,823 to Stokes, et al.; U.S. Pat. No. 6,060,638 to Paul et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes.

The diaper 101 can also include a surge layer 107 that helps to decelerate and diffuse surges or gushes of liquid that can be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface 116 of the bodyside liner 105 and the absorbent core 103. Alternatively, the surge layer 107 can be located on an outwardly facing surface 118 of the bodyside liner 105. The surge layer 107 is typically constructed from highly liquid-permeable materials. Examples of suitable surge layers are described in U.S. Pat. No. 5,486,166 to Ellis, et al. and U.S. Pat. No. 5,490,846 to Ellis, et al., which are incorporated herein in their entirety by reference thereto for all purposes.

The outer cover 117 is typically formed from a material that is substantially impermeable to liquids. For example, the outer cover 117 can be formed from a thin plastic film or other flexible liquid-impermeable material. In one embodiment, the outer cover 117 is formed from a polyethylene film having a thickness of from about 0.01 millimeter to about 0.05 millimeter. The film can be impermeable to liquids, but permeable to gases and water vapor (i.e., "breathable"). This permits vapors to escape from the absorbent core 103, but still prevents liquid exudates from passing through the outer cover 117. If a more cloth-like feeling is desired, the outer cover 117 can be formed from a polyolefin film laminated to a nonwoven web. For example, a stretch-thinned polypropylene film can be thermally laminated to a spunbond web of polypropylene fibers.

Besides the above-mentioned components, the diaper 101 can also contain various other components as is known in the art. For example, the diaper 101 can also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet can be configured to provide a wicking layer that helps to rapidly distribute liquid over the mass of absorbent fibers of the absorbent core 103. The wrapsheet material on one side of the absorbent fibrous mass can be bonded to the wrapsheet located on the opposite side of the fibrous mass to effectively entrap the absorbent core 103. Furthermore, the diaper 101 can also include a ventilation layer (not shown)

that is positioned between the absorbent core 103 and the outer cover 117. When utilized, the ventilation layer can help insulate the outer cover 117 from the absorbent core 103, thereby reducing dampness in the outer cover 117. Examples of such ventilation layers can include a nonwoven web laminated to a breathable film, such as described in U.S. Pat. No. 6,663,611 to Blaney, et al., which is incorporated herein in its entirety by reference thereto for all purposes.

In some embodiments, the diaper 101 can also include a pair of side panels (or ears) (not shown) that extend from the side edges 132 of the diaper 101 into one of the waist regions. The side panels can be integrally formed with a selected diaper component. For example, the side panels can be integrally formed with the outer cover 117 or from the material employed to provide the top surface. In alternative configurations, the side panels can be provided by members connected and assembled to the outer cover 117, the top surface, between the outer cover 117 and top surface, or in various other configurations. If desired, the side panels can be elasticized or otherwise rendered elastomeric by use of the elastic nonwoven composite of the present disclosure. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

As representatively illustrated in FIG. 2, the diaper 101 can also include a pair of containment flaps 112 that are configured to provide a barrier and to contain the lateral flow of body exudates. The containment flaps 112 can be located along the laterally opposed side edges 132 of the bodyside liner 105 adjacent the side edges of the absorbent core 103. The containment flaps 112 can extend longitudinally along the entire length of the absorbent core 103, or can only extend partially along the length of the absorbent core 103. When the containment flaps 112 are shorter in length than the absorbent core 103, they can be selectively positioned anywhere along the side edges 132 of diaper 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704,116 to Enloe, which is incorporated herein in its entirety by reference thereto for all purposes.

To provide improved fit and to help reduce leakage of body exudates, the diaper 101 can be elasticized with suitable elastic members, as further explained below. For example, as representatively illustrated in FIG. 2, the diaper 101 can include leg elastics 106 constructed to operably tension the side margins of the diaper 101 to provide elasticized leg bands which can closely fit around the legs of the wearer to reduce leakage and provide improved comfort and appearance. Waist elastics 108 can also be employed to elasticize the end margins of the diaper 101 to provide elasticized waistbands. The waist elastics 108 are configured to provide a resilient, comfortably close fit around the waist of the wearer.

The diaper 101 can also include one or more fasteners 130. For example, two flexible fasteners 130 are illustrated in FIG. 2 on opposite side edges of waist regions to create a waist opening and a pair of leg openings about the wearer. The shape of the fasteners 130 can generally vary, but can include, for instance, generally rectangular shapes, square shapes, circular shapes, triangular shapes, oval shapes, linear shapes, and so forth. The fasteners can include, for instance, a hook-and-loop material, buttons, pins, snaps, adhesive tape fasteners, cohesives, fabric-and-loop fasteners, etc. In one particular embodiment, each fastener 130 includes a separate piece of hook material affixed to the inside surface of a flexible backing.

The various regions and/or components of the diaper 101 can be assembled together using any known attachment mechanism, such as adhesive, ultrasonic, thermal bonds, etc. Suitable adhesives can include, for instance, hot melt adhesives, pressure-sensitive adhesives, and so forth. When utilized, the adhesive can be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 can be connected to the outer cover 117 using conventional fasteners, such as buttons, hook and loop type fasteners, adhesive tape fasteners, and so forth. Similarly, other diaper components, such as the leg elastic members 106, waist elastic members 108 and fasteners 130, can also be assembled into the diaper 101 using any attachment mechanism.

In general, the devices of the present disclosure can be incorporated into the absorbent article in a variety of different orientations and configurations, so long as the device is capable of receiving urine and providing a signal to a user or caregiver of the USG. For example, the sampling zone and control zone can be visible to the user or caregiver so that a simple, accurate, and rapid indication of USG can be provided. The visibility of such layer(s) can be accomplished in a variety of ways. For example, in some embodiments, the absorbent article can include a transparent or translucent portion 140 (e.g., window, film, etc.) that allows the sampling zone and/or control zone to be readily viewed without removal of the absorbent article from the wearer and/or without disassembly of the absorbent article. In other embodiments, the sampling zone and/or control zone can extend through a hole or aperture in the absorbent article for observation. In still other embodiments, the sampling zone and/or control zone can simply be positioned on a surface of the absorbent article for observation.

Regardless of the particular manner in which it is integrated, urine can be directly discharged to a portion of the sampling zone, a liquid permeable cover or other material surrounding assay device 120, or can be discharged onto a component of the absorbent article into which the assay device 120 has been integrated.

After a sufficient reaction time, the intensity of the color can be measured to quantitatively or semi-quantitatively determine the USG. Nevertheless, while quantitative testing can be performed, qualitative testing is typically employed to provide early testing and monitoring of a health condition. Thus, when a certain USG is detected, the user or caregiver is given an indication that further quantitative testing can be undertaken. For example, a diaper having an integrated assay device can be periodically used with infants or non-ambulatory patients as part of a monitoring program that tests for USG. Upon indication of a sufficiently high USG, further quantitative testing can then be undertaken to determine the scope and stage of the problem detected so a to provide additional treatment information.

Section IV

Empirical Examples

The following empirical examples further illustrate the present invention in detail.

Example 1

A cellulose pad was soaked with 20 mg/ml polyacrylic acid (PAA) at a pH of 7.95 and air-dried. The pad was then soaked with a solution of 2.4% Oasis (surfactant) in 90% ethanol and 10% water and air-dried. The pad was then cut into small pieces (2 cm×4 cm) and to each piece a small drop of 5 mg/ml bromothymol blue in water was applied and allowed to dry. A drop of synthetic urine of different specific gravities was applied to a piece of dipstick to show green, yellowish green, greenish yellow, yellow, yellow and yellow for sample of specific gravities of 1.002, 1.008, 1.014, 1.020, 1.025 and 1.035, respectively.

Example 2

Figure 3:
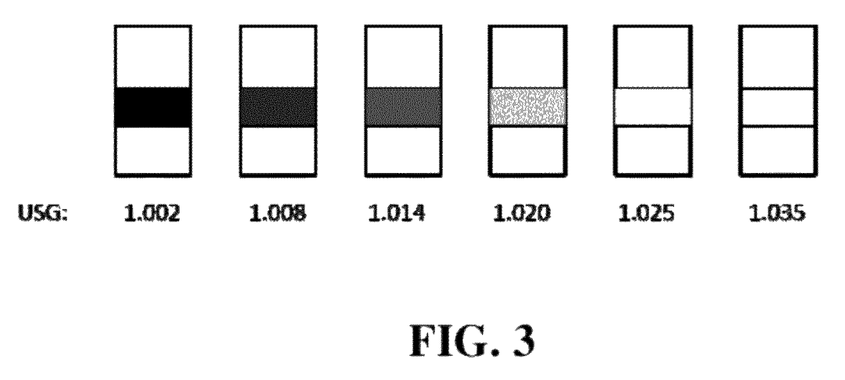
FIG. 3 is a schematic representation of a number of dehydration sensors and their respective change in color when reacted with synthetic urine samples, each at different specific gravity.

A cellulose pad deposited with 20 mg/ml PAA at pH 8.2 was striped with a solution containing 2 ml of 200 mg/ml Oasis (surfactant) and 1 ml of 5 mg/ml bromothymol blue (BTB) and air dried. The pad was cut into 5 mm wide devices to show an initial color of blue. The devices were sealed by Scotch tape except a sample application location. A synthetic urine sample, with specific gravities of 1.002, 1.008, 1.014, 1.020, 1.025 and 1.035, was applied to each device to show green, green, yellow green, greenish yellow, yellow and yellow, respectively, as represented in FIG. 3.

Example 3

A 30 cm long and 4 cm wide cellulose pad deposited with 20 mg/ml PAA at pH 8.2 was soaked with 10 ml solution of 4.8% Oasis (surfactant), 0.1% Tween 20 in water and ethanol (water/ethanol=2/8) and air-dried. The pad was then striped with 5 mg/ml BTB in water/ethanol (7/3) through Kinematic dispenser to make a narrow stripe for the detection zone. The pad was then cut into 5 mm wide devices. The devices were sealed by Scotch tape except a sample application location. A synthetic urine sample, with specific gravities of 1.002, 1.008, 1.014, 1.020, 1.025 and 1.035, was applied to each device to show blue, green, greenish yellow, yellow, yellow and yellow, respectively.

The present invention has been described both generally and in detail by way of examples and the figures. Persons skilled in the art, however, can appreciate that the invention is not limited necessarily to the embodiments specifically disclosed, but that substitutions, modifications, and variations may be made to the present invention and its uses without departing from the spirit and scope of the invention. Therefore, changes should be construed as included herein unless the modifications otherwise depart from the scope of the present invention as defined in the claims.

We claim:

1. An absorbent article capable of determining the ionic strength of urine comprising: a substantially liquid impermeable layer; a liquid permeable layer; an absorbent core positioned between the substantially liquid impermeable layer and the liquid permeable layer; and a lateral flow assay device integrated into the article and positioned such that the device is in fluid communication with the urine when provided by a wearer of the article, the device comprises: a buffering zone, the buffering zone including a polyelectrolyte disposed therein; an detection or indicator zone, the detection zone having a buffering component comprising a weak polymeric acid and weak polymeric base with a pKa $\leq 10^{-3}$, and a charged polymeric surfactant that is responsive to relative ion concentrations in a sample solution, and a charged pH indicator with a charge opposite to that of the charged polymeric surfactant non-diffusively immobilized therein; said charged polymeric surfactant is soluble in amounts of greater than or equal to about 1% by weight ($\geq 1$ wt. % solute) in water and aqueous solutions of low ionic concentration of $\leq 0.1$ wt. % salts, but insoluble ($<1$ wt. % solute) in aqueous solution of high ionic concentrations of $>0.1$ wt. % salts.

2. The absorbent article according to claim 1, wherein said detection zone is largely coterminous with the buffering zone.

3. The absorbent article according to claim 1, wherein said detection zone is separate from the buffering zone and positioned adjacent to and in fluid communication with the buffering zone; with a casing material, the casing material covering at least a portion of the buffering zone and a portion of the indicator zone so as to prevent exposure of such covered portions to the outside environment.

4. The absorbent article according to claim 1, wherein the polyelectrolyte comprises partially neutralized poly(acrylic acid), poly(maleic acid), maleic acid vinyl methyl ether copolymer, poly(methacrylic acid), styrenemaleic acid copolymer, maleic anhydride/methylvinylether copolymer, poly(vinylamine) poly(4-vinylpyridine), or combinations thereof.

5. The absorbent article according to claim 1, wherein the polyelectrolyte is non-diffusively immobilized in the buffering zone.

6. The absorbent article according to claim 1, wherein the pH indicator comprises bromothymol blue, thymol blue, phenol red, neutral red, bromophenol blue, methyl orange, alizarine yellow R, or combinations thereof.

7. The absorbent article according to claim 1, wherein the absorbent article has a transparent or translluent portion in the substantially liquid impermeable layer through which the detection zone is observable.

8. The absorbent article according to claim 3, wherein the casing material defines an opening, the opening configured to allow air to pass through it as urine passes through the device.

* * * * *